(12) United States Patent
Youcheff et al.

(10) Patent No.: US 6,635,303 B1
(45) Date of Patent: Oct. 21, 2003

(54) POWDERED MILK SOLIDS FOR PROVIDING A DEVELOPED MILK FLAVOR TO CHOCOLATE, THE METHOD OF PREPARATION AND CHOCOLATE PREPARED WITH THE SAME

(75) Inventors: Gary Youcheff, Maytown, PA (US); Janice M. Johnson, Landisville, PA (US); Neil A. Willcocks, Flanders, NJ (US)

(73) Assignee: Hawley & Hoops, Inc., McLean, VA (US)

( * ) Notice: Subject to any disclaimer, the term of this patent is extended or adjusted under 35 U.S.C. 154(b) by 242 days.

(21) Appl. No.: 09/897,677

(22) Filed: Jul. 2, 2001

Related U.S. Application Data

(60) Provisional application No. 60/215,750, filed on Jun. 30, 2000.

(51) Int. Cl.[7] .............................. A23C 1/00; A23G 1/00; A23L 1/221
(52) U.S. Cl. ...................... 426/588; 426/34; 426/631; 426/533
(58) Field of Search ................... 426/588, 631, 426/34, 533

(56) References Cited

U.S. PATENT DOCUMENTS

| | | | | |
|---|---|---|---|---|
| 1,966,460 A | * | 7/1934 | Otting ........................ 426/35 |
| 2,638,418 A | * | 5/1953 | Kempf et al. .................. 426/35 |
| 2,794,743 A | * | 6/1957 | Farnmah ...................... 426/63 |
| 2,835,593 A | * | 5/1958 | Rusoff ......................... 426/35 |
| 4,081,568 A | * | 3/1978 | Bracco ........................ 426/584 |
| 4,418,091 A | * | 11/1983 | Glas ........................... 426/580 |
| 4,826,693 A | * | 5/1989 | Smith et al. .................... 426/34 |
| 5,393,538 A | * | 2/1995 | Chmiel et al. ................. 426/35 |
| 5,676,993 A | * | 10/1997 | Watterson et al. ........... 426/533 |
| 5,695,802 A | * | 12/1997 | Van Den Ouweland et al. . 426/533 |
| 6,242,015 B1 | * | 6/2001 | Egi et al. ...................... 426/34 |
| 6,287,620 B1 | * | 9/2001 | Van Den Ouweland et al. . 426/534 |
| 2002/0034570 A1 | * | 3/2002 | Krammer et al. ........... 426/534 |

FOREIGN PATENT DOCUMENTS

JP     403004747    *   1/1991

* cited by examiner

*Primary Examiner*—Carolyn Paden
(74) *Attorney, Agent, or Firm*—Fitzpatrick, Cella, Harper & Scinto

(57) ABSTRACT

Powdered milk solids are disclosed having a free fatty acid profile that provides for a developed milk character when used to prepare milk chocolate. Methods of preparing the powdered milk solid and preparing milk chocolate with the powdered milk solids are also disclosed. Novel chocolates having a developed milk character are also disclosed.

47 Claims, No Drawings

POWDERED MILK SOLIDS FOR PROVIDING A DEVELOPED MILK FLAVOR TO CHOCOLATE, THE METHOD OF PREPARATION AND CHOCOLATE PREPARED WITH THE SAME

This application claims the benefit of U.S. Provisional Patent Application No. 60/215,750, filed Jun. 30, 2000

BACKGROUND OF THE INVENTION

1. Field of the Invention

This invention is related to powdered milk solids having a specific free fatty acid profile that may be used to prepare chocolate having a flavor profile with a developed milk character, which may be described as having a cheesy, soured and perceived "soapy" character. The invention is also directed to a method of preparing such powdered milk solids by enzymatic modification, a method of preparing chocolate using the powdered milk solids and the chocolate prepared thereby.

2. Related Background Art

It has long been known that the flavor profile of milk chocolate can vary. Many attempts have been made to control this variability and consistently achieve a particular flavor profile. For example, U.S. Pat. No. 1,966,460 is directed to the preparation of milk-containing products, such as milk chocolate, with a distinctive milk or butter flavor by adding lipolyzed butter fat to the milk solids used in the milk-containing product. The success of this method, however, is challenged in U.S. Pat. No. 2,794,743 which alleges that the process of U.S. Pat. No. 1,966,460 resulted in "off" flavors.

This problem is alleged to have been overcome in U.S. Pat. No. 2,794,743 by using an enzyme composition having both lipolytic and proteolytic qualities for modifying milk powder. In particular an enzyme powder is employed that is said to produce relatively higher levels of C6 and higher fatty acids compared to the level of C4 and lower acids, but where the level of C4 free fatty acid is greater than the other lower fatty acids. The enzyme powder is added to whole milk powder in amounts up to 50%, preferably 1% to 5%, to obtain milk chocolate with a modified flavor. The exemplified milk powders all have a C4 to C6 and higher fatty acid percentage ratio greater than 1:2.

U.S. Pat. No. 2,638,418 is directed to the preparation of a milk product that imparts a desirable flavor to milk chocolate by hydrolyzing milk fat and reducing two of three categories of free fatty acids. The categories are described as volatile water-soluble free fatty acids, volatile water-insoluble free fatty acids and non-volatile water-insoluble free fatty acids. It is stated that the first two categories of free fatty acids should be present in slight excess to the free fatty acids of the third category. There is, however, no disclosure of the specific fatty acid profile of the milk fat. Moreover, in tests conducted by the present inventors it was found that under certain high temperature and pressure conditions (e.g. 140° C. and 47 psi) the ratio of C4:C14 in milk powder actually increased.

U.S. Pat. No. 2,835,593 describes the preparation of a base flavor by enzymatic hydrolysis of milk fat and protein. The base flavor may be used to prepare an artificial chocolate or to modify the flavor of chocolate. It is alleged that the base flavor contains buttery aromas suggestive of the cowy butyral character desired in milk chocolate. The specific fatty acid profile of the flavor is not disclosed.

Acceleration of the lipolysis in milk powder for use in milk chocolate is described in U.S. Pat. No. 4,081,568. The technique is performed by adjusting the pH of the mixture of ingredients used to produce milk chocolate. The lipolysis generally results in 2.4 to 2.5% by weight of free fatty acids based on total fat. Again there is no specific disclosure of the free fatty acid profile.

A crumb-flavored milk chocolate composition prepared by adding fatty acids to milk powder at a temperature below the melting point of the fatty acids and then using the mixture in the manufacture of milk chocolate is described in U.S. Pat. No. 5,393,538. The product may also be prepared by lipolysis of the milk powder to preferentially produce long chain fatty acids.

Milk solids powders that have the specific free fatty acid profile described herein and that consistently provide the desirable developed milk flavor provided for by the present invention in the production of chocolate are not disclosed or suggested in the above-noted references. The phrase "developed milk flavor" as used herein means a chocolate that organoleptically may be described as having aromatic characteristics of fermented and enzymatically altered milk products such as cheese and/or sour aromatic associated with "milk bottle" odor. Aromatic sour is associated with fermented and enzymatically altered milk products such as yogurt, sour cream and buttermilk. Accordingly, a milk solids powder that would consistently provide such developed milk flavor to chocolate would be highly desirable.

SUMMARY OF THE INVENTION

This invention is related to a powdered milk solids that may be used in the preparation of chocolate, most preferably milk chocolate, to provide a product having a desirable developed milk character. In particular, the powdered milk solids of this invention has a free fatty acid profile wherein the weight ratio of butyric acid (C4) to myristic acid (C14) is equal to or less than 1:2, preferably in a range of 1:2 to 1:10,000, more preferably 1:2.5 to 1:100, even more preferably 1:3 to 1:10 and most preferably 1:3 to 1:6.

The invention is also related to the methods of preparing the powdered milk solids having the above described fatty acid profile. This can be achieved by several different methods. For example, the milk powder may be prepared by adding the desired fatty acid(s) to a conventional untreated milk and drying the same to obtain a milk powder having the required C4 to C14 fatty acid profile. Alternatively, the desired fatty acids may be added at the preferred levels indirectly to any of the chocolate ingredients contained in a chocolate or coating formulation or directly into a liquid finished chocolate product. Addition in this manner is possible with careful addition of the fatty acids and with sufficient blending to assure proper dispersion either to a liquid or dry powder chocolate ingredient. Some fatty acids are volatile components. As such overheating and volatilization of these compounds may result in loss of the flavorants. Dispersion may be carried out using high shear mixers, during batching, conching, liquefaction or standardizing using all known conventional blending equipment. Fatty acids as described herein may be derived from any known means. Typically, fatty acids may be sourced from natural sources via extraction or synthetically produced by enzyme addition or chemical means.

In another embodiment, the milk powder of this invention can be prepared by treating a conventional enzymatically treated milk powder with vacuum to reduce the C4 concentration to achieve the desired C4 to C14 weight ratio. Yet another manner of preparing the milk powder of this invention includes enzymatically modifying a liquid milk to directly obtain a milk having the required C4 to C14 ratio. As used herein, the phrase "liquid milk" includes milk, reconstituted milk, partially reconstituted milk, evaporated milk, condensed milk, recombined milk, i.e., milk reassembled from milk components, skim milk containing one or more of milk fat, anhydrous milk fat, milk fat equivalents and butter, and mixtures thereof. It may also be possible to spray dry a cultured milk to obtain the powdered milk solids of the invention.

Yet another embodiment of this invention includes enzymatically treating milk fat, anhydrous milk fat or butter to achieve the desired weight ratio of C4 to C14 or alternatively to remove undesirable fatty acids through steam distillation to achieve the desired C4 to C14 weight ratio. The resultant milk fat or butter may be added to the admixture used to prepare chocolate so as to obtain a chocolate having the required C4 to C14 weight ratio.

Yet another embodiment of this invention is directed to the method of preparing a chocolate having developed milk character by mixing (i) the powdered milk solids of this invention, (ii) optionally, but preferably, cocoa butter, (iii) cocoa solids and/or chocolate liquor and (iv) sugar. If desired, the chocolate prepared thereby may also include milk and/or milk solids that have not been enzymatically modified so long as the powdered milk solids of this invention are present in an amount effective to impart a developed milk character to the chocolate.

A further embodiment of this invention is directed to a method of preparing a chocolate having developed milk character comprising the steps of: (i) admixing a liquid milk with at least one of sugar, chocolate liquor, cocoa solids or cocoa butter to form a liquid chocolate precursor ingredient; (ii) modifying the liquid chocolate precursor ingredient to achieve a C4 to C14 ratio equal to or less than 1:2; (iii) drying the liquid chocolate precursor ingredient; and (iv) preparing the chocolate with the dried chocolate precursor ingredient. The method of modifying the liquid chocolate precursor ingredient may be performed using any of the fatty acid profile modification techniques described herein. The step of drying is preferably spray drying. Preferably, sugar and/or chocolate liquor are added to liquid milk to form the liquid chocolate precursor ingredient. After drying, any additional ingredients desired, including any ingredients used to form the liquid chocolate precursor ingredient, are added to the dry chocolate precursor ingredient to complete the chocolate.

DETAILED DESCRIPTION OF THE INVENTION

This invention provides powdered milk solids which may be advantageously used to produce chocolate having a desirable developed milk character. The developed milk character may be described through sensory evaluations as providing a soapy, and even cheesy flavor profile. Most preferably the chocolate prepared using the powdered milk solids of this invention is a milk chocolate. Commercially available milk chocolate exhibiting such a flavor profile is well known. It is not believed, however, that powdered milk solids are used in the production of that milk chocolate. Significantly, the powdered milk solids of this invention provides one the ability to consistently obtain a chocolate having a developed milk character.

The consistency of the flavor profile achieved using the milk powder of this invention in the preparation of milk chocolate is dependent upon the free fatty acid profile of the milk solids used in the chocolate. In particular, it has been discovered that milk chocolate having a developed milk character can be produced using powdered milk solids having a free fatty acid profile wherein the weight ratio of butyric acid (C4) to myristic acid (C14) is equal to or less than 1:2, preferably the weight ratio is in a range of 1:2 to 1:10,000, more preferably 1:2.5 to 1:100, even more preferably 1:3 to 1:10 and most preferably 1:3 to 1:6.

This can be achieved by several different methods. For example, the milk powder may be prepared by adding the desired fatty acid(s) to a conventional untreated milk and drying the same to obtain a milk powder having the required C4 to C14 fatty acid profile. Alternatively, the desired fatty acids may be added at the preferred levels indirectly to any of the chocolate ingredients contained in a chocolate or coating formulation or directly into a liquid finished chocolate product. Addition in this manner is possible with careful addition of the fatty acids and with sufficient blending to assure proper dispersion either to a liquid or dry powder chocolate ingredient. Some fatty acids are volatile components. As such overheating and volitization of these compounds may result in loss of the flavorants. Dispersion may be carried out using high shear mixers, during batching, conching, liquefaction or standardizing using all known convention blending equipment. Fatty acids as described herein may be derived from any known source. Typically, fatty acids may be sourced from natural sources via extraction or synthetically produced by enzyme addition or chemical means.

Chocolate as defined herein may be a standardized chocolate such as sweet, mixed dairy, skim milk, or a non-standardized product such as compound coatings which contain vegetable fats replacing some or all of the cocoa butter.

The concentration of the fatty acids in the milk powder of this invention may vary, so long as the required ratio of butyric acid to myristic acid is met. For example, if the dairy component of a chocolate is derived solely from the milk solids of this invention then the concentration of the fatty acids need not be as high as would be required where only a portion of the dairy component of a chocolate was derived from the milk solids of this invention. Generally, the concentration of free fatty acids found in the milk solids of this invention will range as follows:

| | |
|---|---|
| butyric acid | 45 ppm to 7,300 ppm, preferably 90 ppm to 900 ppm |
| caproic acid | 37 ppm to 3,500 ppm, preferably 75 ppm to 750 ppm |
| caprylic acid | 32 ppm to 1,300 ppm, preferably 65 ppm to 650 ppm |
| capric acid | 70 ppm to 3,400 ppm, preferably 140 ppm to 1,400 ppm |
| lauric acid | 80 ppm to 4,100 ppm, preferably 160 ppm to 1,600 ppm |
| myristic acid | 227 ppm to 14,600 ppm, preferably 455 ppm to 4,550 ppm |

If the milk solids of this invention is the predominant dairy component in the chocolate then the concentration of the fatty acids will generally be toward the lower end of the above-described ranges. However, if only a portion of the dairy component of the chocolate is provided by the milk solids of this invention, e.g. 10%, then the concentration of free fatty acids in the inventive milk solids will generally gravitate towards the higher end of the above-described ranges.

The powdered milk solids may be prepared in any manner that provides a powdered milk solids with a C4 to C14 weight ratio equal to or less than 1:2. One technique to prepare the powdered milk solids of this invention comprises the step of adding an effective amount of myristic acid (C14) to untreated liquid milk to achieve a C4 to C14 weight ratio equal to or less than 1:2. Conventional enzyme treated liquid milk generally has a C4 to C14 weight ratio of about 1:1. The amount of myristic acid necessary to achieve the desired ratio can be readily ascertained by analytical analysis of the untreated liquid milk. The liquid milk containing the additional myristic acid is then dried using conventional drying techniques, such as spray drying or freeze drying, to result in the powdered milk solids of this invention.

Another technique for preparing the powdered milk solids of this invention includes first using a conventional enzymatic modification method on liquid milk. Such known enzymatically treated liquid milk have C4 to C14 ratios greater than those of the present invention. Exemplary enzymatically treated powdered milks include NDF™ Kosher Whole Milk Flavor (SKW Biosystems, Waukesha, Wis.) and NATURETONE 3968 (Kerry Inc., Beloit, Wis.).

The enzymatically modified liquid milk or powdered milk is then further treated to reduce the C4 fatty acid level to achieve the above-described free fatty acid profile. This further treatment may include, for example, the use of vacuum-techniques well known to those skilled in the art to draw off the more volatile C4 fatty acid in a greater percentage than the C14 fatty acid. The powdered milk solids of this invention are recovered from the modified liquid milk by well known drying techniques, such as spray drying or freeze drying.

Another method of this invention is directed to preparing the milk powder of this invention by enzymatically modifying a liquid milk to directly obtain a milk having the required C4 to C14 ratio. Various microbial cultures may be used for enzymatically modifying liquid milk in the methods of this invention. Generally such microbial cultures may be sourced from food grade microbial genuses such as, for example, Mucor variants, Rhizopus variants, Aspergillus variants, Candida variants and Penicillin variants. More specifically exemplary variants include *Mucor javanicus, Rhizopus oryzae, Aspergillus niger, Candida rugosa* and *Penicillin roqueforti*. It is also possible to enzymatically modify milk using food grade enzymes sources from animals such as edible forestomach tissue of calves, kids or lambs or from animal pancreatic tissue.

Yet another embodiment of this invention is directed to a method of preparing chocolate, most preferably milk chocolate, using the powdered milk solids having the free fatty acid profile described herein in an amount effective to provide the milk chocolate with a developed milk character. This method of preparing chocolate comprises mixing sugar, optionally, but preferably, cocoa butter, cocoa solids and/or chocolate liquor and the powdered milk solids of this invention. If desired unmodified milk solids or modified milk solids having the C4 to C14 weight ratio greater than 1:2 may be used in combination with the milk solids of this invention in the method of preparing chocolate so long as the resulting chocolate maintains a C4 to C14 weight ratio equal to or less than 1:2, and preferably in a range of 1:2 to 1:10,000, more preferably 1:2.5 to 1:100, even more preferably 1:3 to 1:10 and most preferably 1:3 to 1:6. This C4 to C14 weight ratio may also be obtained by adding myristic acid directly to the admixture of ingredients used to prepare chocolate.

It is also possible to prepare a chocolate according to the method of this invention using enzymatically treated milk fat, anhydrous milk fat or butter with the desired ratio of C4 to C14. Milk fat, anhydrous milk fat or butter having the desired ratio of C4 to C14 prepared by removing undesirable fatty acids through steam distillation may also be employed. These components may be used alone or in combination with any other components in the chocolate prepared according to this invention so long as the required C4 to C14 ratio is obtained in the resulting chocolate. It should also be readily apparent that the process of this invention also includes reconstituting a milk powder, either wholly or partially, treating the reconstituted milk powder to achieve the desired ratio of C4 to C14 and then drying the treated reconstituted milk powder to form the powdered milk solids used in the preparation of chocolate.

Another embodiment of this invention is directed to the chocolate prepared by the above-described methods of this invention. Chocolates can be manufactured using the powdered milk solids of this invention over a wide range of potential ingredient usage levels that encompass the following ranges:

| | |
|---|---|
| Nutritive Carbohydrate Sweeteners | 30% to 70% |
| Chocolate Liquor | 10% to 60% |
| Cocoa Butter | 0% to 30% |
| Powdered Milk Solids of the Invention | 1% to 40% |
| Non Fat Milk Solids | 0% to 30% |
| Milk Fat | 0% to 10% |

Other suitable ingredients can be added for desired flavor and functionality. Once the chocolate components have been admixed, forming the chocolate is well within the knowledge of those skilled in the art via such known techniques as conching and refining the chocolate components.

The chocolate of this invention will have a C4 to C14 weight ratio equal to or less than 1:2, and preferably in a range of 1:2 to 1:10,000, more preferably 1:2.5 to 1:100, even more preferably 1:3 to 1:10 and most preferably 1:3 to 1:6. Generally, the chocolate of this invention will contain at least 35 mg of butyric acid per kilogram of chocolate and at least 70 mg of myristic acid per kilogram of chocolate, as well as meeting the weight ratio profile defined above. The amounts of milk powder, sugar, cocoa butter and cocoa solids found in the chocolate of this invention has been previously described in the method used to prepare the chocolate.

A chocolate of this invention having about 12% whole milk solids (including nonfat solids and milk fat) will generally have a concentration of free fatty acids as follows:

| | |
|---|---|
| butyric | 5 ppm to 876 ppm, preferably 11 ppm to 100 ppm |
| caproic acid | 4 ppm to 420 ppm, preferably 9 ppm to 89 ppm |
| caprylic acid | 4 ppm to 156 ppm, preferably 8 ppm to 77 ppm |
| capric acid | 8 ppm to 408 ppm, preferably 17 to 168 ppm |
| lauric acid | 10 ppm to 492 ppm, preferably 19 ppm to 192 ppm |
| myristic acid | 27 ppm to 1752 ppm, preferably 55 ppm to 545 ppm |

While the manipulation of butyric acid and myristic acid have been described in detail herein, one should recognize that other fatty acids, such as caproic, caprylic, capric and lauric acid, may be added or reduced in the milk powder or chocolate of this invention to achieve a desired concentration and a product with a developed milk character.

The chocolate of this invention prepared using the powdered milk solids of this invention may be distinguished from chocolate prepared with liquid milk by the crystal structure of the lactose in the chocolate. Chocolates prepared via a wet milk system show various forms of re-crystallized alpha mono-hydrate lactose, primarily in cubed, partial cube or partial wedge configuration when viewed using polarized light microscopy. This crystalline form of lactose is substantially absent in chocolate prepared using the powdered milk solids of this invention. The chocolate of this invention may also be differentiated from chocolate prepared with liquid milk by the crystal structure of sucrose in the chocolate. Chocolate prepared using liquid milk will contain re-crystallized sucrose having a monoclinic structure while the sucrose in the chocolate of this invention will contain predominantly fractured crystal sucrose. This difference in sugar crystal morphology may also be evaluated by using microchemical techniques that include photomicroscopy analysis involving birefringence and retardation spectra.

More particularly, sucrose and lactose occur primarily in two solid phase states. These consist of two distinctly different formations and are defined by the packing structure of the unit cells. One phase state is crystalline, which exhibits uniform packing of the crystal lattice. The other solid phase condition is amorphous; in which the unit cells are randomly aligned forming a glassy state lattice. Sucrose, assuming the supporting conditions are available, forms a well-defined monoclinic crystal formation. Under less ideal crystal growth conditions, sucrose will form cubes or partial cubes, but are still crystalline based on the spatial arrangement of the unit cells. These monoclinic or cubed structures can be identified using cross-polar light microscopy (CPLM) techniques and exhibit unique birefringence and retardation [optical density] characteristics under cross-polar light. Lactose will also form discrete crystals in the form of wedge or tomahawk like shapes under ideal conditions and partial wedges or cubes under poor conditions. Due to these differences in molecular densities, shape and optical rotation of crystalline sucrose and lactose, micro-chemical and morphological characterization using CPLM techniques can identify these compounds and their structures very readily. Amorphous sugars, [sucrose, lactose] due to the randomness or order of their unit cells, exhibit different birefringence characteristics than their crystalline forms. Sucrose and lactose will form a glass or amorphous structure if the moisture level is high enough to support dissolution. The release of water and small amounts of energy in the form of heat [latent heat of crystallization] occur during glassy state to crystalline transitions.

In addition to the CPLM techniques described above, differential scanning calorimetry (DSC) can differentiate between crystalline and amorphous sugars. A shift in endothermic response occurs when amorphous sugars are pushed through their glass transition [Tg] temperature and exhibits exothermal response during recrystallization. These glass transition and recrystallization events occur at different temperatures for sucrose and lactose depending on Aw or sorption state. Quantitative levels of amorphous sucrose will exist in wet milk and wet system type processes [reconstituted], and will be essentially non existent in dry system processes.

In a wet milk process, liquid whole milk or sweetened condensed milk is condensed by an evaporation process driving off moisture by heat and sometimes vacuum. Sucrose [crystalline] and possibly chocolate liquor is added to this process to facilitate drying, flavor and recipe development. Saturation or super saturation of the milk/sugar solution occurs at around 60–70% depending on temperature with the result of some crystalline sucrose precipitating out. The majority of sucrose however is converted to the amorphous state, much of which survives the heat drying and milling process. It is due to this reason that the above mentioned techniques make differentiation possible of the chocolate of this invention from commercially available chocolate prepared via a liquid milk process.

The examples which follow illustrate preferred embodiments of the present invention and are not meant to limit the scope of this invention in any way.

EXAMPLE 1

A milk powder of this invention is prepared as follows:
Raw milk is pasteurized using the appropriate time temperature relationships stated by the U.S. Public Health Service (Table 1) to destroy pathogenic microorganisms and inactivate enzymes in milk.

TABLE 1

| Time-temperature conditions for pasteurizing whole milk | |
|---|---|
| Minimum Temperature (° C.) | Minimum Time (seconds) |
| 62.8 | 1800 (30 min) |
| 71.7 | 15 |
| 88.3 | 1 |
| 90.0 | 0.5 |
| 93.9 | 0.1 |
| 95.6 | 0.05 |
| 100 (HTST) | 0.01 |
| 138 (UHT) | 2 |

HTST = high temperature short time
UHT = ultra high temperature

Milk products with added sweeteners and extra butterfat are typically pasteurized, for example, at 65.5° C. for 30 minutes or 74° C. for 15 sec. For cultured milk products, operation conditions are generally 74° C. for 30 minutes or 90° C. for 5 minutes.

Ingestion of certain feeds by the cow may result in undesirable flavors in the milk that must be removed for quality acceptance. Therefore, a combination of steam injection/infusion and vacuum flash evaporation process is optimally used to successfully remove the off-note. Steam under pressure is injected directly into the milk while maintaining a vacuum of about 20 inches of mercury. The process is designed to remove the water added by the injection/infusion of the steam. Therefore the composition of the milk remains unchanged. The temperature of the milk is generally set to a maximum temperature, which does not alter the desired characteristics of the milk.

Excess water is optionally removed from the milk achieving a total solids content up to about 40%. Water removal is accomplished by evaporation (atmospheric and reduced pressure) or by freeze concentration. Alternatively, milk solids are added to increase the total solids content. Typical vacuum evaporation temperatures are $\leq 50°$ C. to preserve the chemical and physiochemical properties of the milk. Evaporators that are used include standard, single or multiple effect, falling-film, thin-film (with vacuum, 23–28 in Hg) and centrifugal.

To increase the lipolytic enzyme action, the milk fat globule surface area is preferably increased through homogenization. Globule sizes generally range from 1 to 15 micrometers and are reduced to approximately one micrometer in size after homogenization. Typical homogenization conditions are ≧60° C. (temperatures where the fat is fluid) and through a one or two stage process at combined pressures of 120 to 176 kg/cm².

Hydrolysis of fatty acids from glycerol backbone is accomplished by the addition of lipases or by holding the milk at or near refrigeration temperature for 24 to 48 hours prior to pasteurization to promote hydrolysis by indigenous enzymes, a technique commonly known by those skilled in the art. Sources of food grade enzymes include animal (edible forestomach tissue of calves, kids, or lambs or from animal pancreatic tissue) and microbial (*Aspergillus niger* var., *Rhizopus niveus, Mucor miehei* var.). Typical incubation temperatures range from 30–60° C. and incubation time is largely dependent on enzyme activity, temperature and degree of agitation. Agitation will increase the rate of hydrolysis and therefore decrease the incubation time. Agitation maybe achieved by mechanical stirring or by recirculating the milk via a centrifugal pump. The ratio of C4:C14 in milk powder may also be modified through direct addition of food grade enzymes or active cultures under controlled conditions. Typical conditions for optimal lipase activity are 25–60° C. and pH 5.5–8.5 with an enzyme addition of 0.01–1% of the amount of fat containing milk raw material depending on the choice of enzyme. Higher levels may be added to accelerate the enzyme reaction. For example, up to 0.4% commercially available microbial lipases From *Mucor javanicus* (Lipase M. "Amano" 10) and *Rhizomucor miehei* (FAP-15) both available from Amano Enzyme USA, Lombardo, Ill., and *Rhizomucor miehei* (Palatase®), available from Novozyme, Franklinton, N.C. were added to whole milk and incubated at 40–45° C. with an average stir rate of 15 rpm. Each milk was heated to greater than 90° C. for 1 minute and freeze dried to produce a palatable milk powder with a maximum of 10% hydrolyzed total fat (based on oleic acid). The C4:C14 ratios, were calculated from High Pressure Liquid Chromatography (HPLC) results (Elliott et al., 1989) Lipase M, FAP-15 and Palatase® milkpowders, had a C4:C14 ratio of 0.12, 0.07 and 0.02, respectively. The fatty acid results for these powders are set out in the table below.

Fatty acid concentration (ppm) in whole milk powder treated with various lipases.

| Fatty acid | FAP-15 (ppm) | "Amano" 10 (ppm) | Palatase ® (ppm) |
|---|---|---|---|
| C4 | 545 | 131 | 31 |
| C6 | 582 | 135 | 145 |
| C8 | 481 | 203 | 87 |
| C10 | 765 | 226 | 142 |
| C12 | 1148 | 443 | 337 |
| C14 | 4530 | 1887 | 1573 |

Once the desired level of free fatty acids is achieved, the enzymes are inactivated to prevent further hydrolysis. Enzyme inactivation is generally achieved through a second pasteurization step using the time-temperature relationship shown in Table 1.

Prior to spray drying, the enzyme treated milk is concentrated to a solid concentration ranging between 40–60%. Typical evaporator temperatures are less than 70° C. with sufficient vacuum to boil milk at the operating temperature. Employing high temperatures (100–140° C.) and vacuum (28–30 in Hg) will also remove some of the liberated free fatty acids from the milk with shorter chain fatty acids (C4 to C 10) having the greatest loss compared to medium and long chain fatty acids. The temperature and pressure operating conditions are used to determine the fatty acid profile and a milk having a butyric acid to myristic acid weight ratio equal to or less than 1:2 is obtained.

The treated milk is atomized by pumps and pressure nozzle systems with pressure ranging from 141 to 281 kg/cm². Large volumes of heated milk are pumped at inlet temperatures in the range of 163 to 204° C. through the spray drier with an outlet air temperature between 38 and 49° C. Dried product is promptly cooled, degassed, and stored under vacuum or inert atmosphere to inhibit development of stale and oxidized off-flavors. The spray dried milk product will have a typical moisture concentration ≧4%.

EXAMPLE 2

A chocolate with developed milk character using an enzyme modified milk powder of this invention is prepared. The weight ratio of butyric acid to myristic acid in the enzyme modified milk powder is less than 1:2 and the free fatty acid are quantitatively present at levels that allow for the use of the milk powder as the entire dairy component for this chocolate. The following ingredients are used:

|  | % w/w |
|---|---|
| Sucrose | 47.23 |
| Chocolate Liquor | 16.6 |
| Cocoa Butter | 15.37 |
| enzyme Modified Milk Powder | 20.29 |
| Lecithin | 0.49 |
| Vanillin | 0.02 |

The chocolate is prepared by blending all dry ingredients, including the enzyme modified milk powder, and a portion of the cocoa butter necessary to achieve the proper consistency for refining. The mass is then conched according to known procedures. The fat and lecithin are added at the final stage of manufacture to make the mass fluid. The resulting chocolate has a developed milk character.

EXAMPLE 3

A chocolate with developed milk character is prepared using an enzyme modified milk powder of this invention. The weight ratio of butyric acid to myristic acid is less than 1:2 in the enzyme modified milk powder and the free fatty acids are quantitatively present at levels that allow for the use of the milk as a supplement of the dairy component for this chocolate to result in the desired level of specialized flavor. The following ingredients are used.

|  | % w/w |
|---|---|
| Sucrose | 44.87 |
| Chocolate Liquor | 15.77 |
| Cocoa Butter | 14.60 |
| Whole Milk Solids | 19.28 |
| Lecithin | 0.47 |
| Vanillin | 0.02 |
| Enzyme Modified Milk Powder | 5.00 |

The chocolate is prepared by blending all dry ingredients, including the enzyme modified milk, and a portion of the cocoa butter necessary to achieve the proper consistency for refining. The mass is then conched according to known procedure. The fat and lecithin are added at the final stage of manufacture to make the mass fluid. The resulting chocolate has a developed milk character.

Samples of a commercially available milk chocolate believed to be produced with a liquid milk and a chocolate prepared with the enzyme modified milk of this invention were analyzed by DSC to determine the differences in amorphous content. Samples were acetone extracted to remove fat and dried in a desiccator with phosphorous pentoxide $P_2O_5$ and Drierite ($CaSO_4$—$CoCl_2$) for 7 days. Acetone was used because of its polarity [its ability to prevent dissolution of crystalline sugars]. Samples were placed in a DSC and scanned from 40 c to 200 c at 5/min. Re-crystallization exotherms were integrated and compared against technical grade amorphous and crystalline sucrose for quantification. Chocolates prepared with the enzyme modified milk of this invention generally exhibited <3% maximum levels of amorphous sucrose with results typically in the 1–1.5% range, while the commercially available milk chocolate showed amorphous sucrose levels in the 7–15% range, and typically about 10–12%.

What is claimed is:

1. Powdered milk solids having a free fatty acid profile wherein the weight ratio of butyric acid to myristic acid is equal to or less than 1:2.

2. The powdered milk solids according to claim 1, wherein said weight ratio of butyric acid to myristic acid is in a range of 1:2.5 to 1:100.

3. The powdered milk solids according to claim 1, wherein said weight ratio of butyric acid to myristic acid is in a range of 1:3 to 1:6.

4. The powdered milk solids according to claim 1, wherein said free fatty acid profile comprises:
   (i) butyric acid in a range of about 45 ppm to about 7,300 ppm;
   (ii) caproic acid in a range of about 37 ppm to about 3,500 ppm;
   (iii) caprylic acid in a range of about 32 ppm to about 1,300 ppm;
   (iv) capric acid in a range of about 70 ppm to about 3,400 ppm;
   (v) lauric acid in a range of about 80 ppm to about 4,100 ppm; and
   (iv) myristic acid in a range of about 227 ppm to about 14,600 ppm.

5. The powdered milk solids according to claim 1, wherein said free fatty acid profile comprises:
   (i) butyric acid in a range of about 90 ppm to about 900 ppm;
   (ii) caproic acid in a range of about 75 ppm to about 750 ppm;
   (iii) caprylic acid in a range of about 65 ppm to about 650 ppm;
   (iv) capric acid in a range of about 140 ppm to about 1,400 ppm;
   (v) lauric acid in a range of about 160 ppm to about 1,600 ppm; and
   (iv) myristic acid in a range of about 455 ppm to about 4,550 ppm.

6. A process for preparing a powdered milk solids for use in flavoring milk chocolate, said process comprising the steps of;
   (a) enzymatically modifying a liquid milk to form a modified milk product;
   (b) treating the modified milk product to reduce an amount of butyric acid and achieve a weight ratio of butyric acid to myristic acid that is equal to or less than 1:2; and
   (c) drying to recover the powdered milk solids from said treated modified milk product.

7. The process according to claim 6, wherein said weight ratio of butyric acid to myristic acid is in a range of 1:2.5 to 1:100.

8. The process according to claim 6, wherein said weight ratio of butyric acid to myristic acid is in a range of 1:3 to 1:6.

9. The process according to claim 6, wherein said liquid milk is selected from the group consisting of (i) milk, (ii) reconstituted milk, (iii) partially reconstituted milk, (iv) evaporated milk, (v) condensed milk, (vi) recombined milk, (vii) skim milk containing one or more of milk fat, anhydrous milk fat, milk fat equivalents and butter, and (viii) mixtures thereof.

10. The process according to claim 6, wherein the step of enzymatic modification comprises contacting the liquid milk with a microbial culture.

11. The process according to claim 10, wherein the microbial culture is selected from the group consisting of Mucor variants, Rhizopus variants, Aspergillus variants, Candida variants and Penicillium variants.

12. The process according to claim 6, wherein the step of treating the modified milk product comprises vacuum distillation.

13. The process according to claim 6, wherein the step of recovering the powdered milk solids comprises spray drying or freeze drying.

14. A process for preparing chocolate having a developed milk flavor comprising the steps of admixing (i) sugar, (ii) optionally cocoa butter, (iii) cocoa solids or chocolate liquor and (iv) powdered milk solids and forming said chocolate having a developed milk flavor from said admixture, wherein the chocolate has a free fatty acid profile with a weight ratio of butyric acid to myristic acid equal to or less than 1:2.

15. The process according to claim 14, wherein (i) said sugar is used in an amount in a range of about 30% to about 70% by weight of the chocolate; (ii) said cocoa butter is used in an amount in a range of about 0% to about 30% by weight of the chocolate; (iii) said cocoa solids or chocolate liquor is used in an amount in a range of about 10% to about 60% by weight of the chocolate; and (iv) said powdered milk solids is used in an amount in a range of about 1% to about 40% by weight of the chocolate.

16. The process according to claim 14, wherein said weight ratio of butyric acid to myristic acid is in a range of 1:2.5 to 1:100.

17. The process according to claim 14, wherein said weight ratio of butyric acid to myristic acid is in a range of 1:3 to 1:6.

18. The process according to claim 14, wherein said admixture further comprises a powdered milk solids having a butyric to myristic weight ratio less than 1:2.

19. The process according to claim 14, further comprising the steps of (i) reconstituting or partially reconstituting milk solids to form a reconstituted milk solids; (ii) treating the reconstituted milk solids to achieve a butyric to myristic weight ratio equal to or less than 1:2; and (iii) drying said treated reconstituted milk solids to form a powdered milk solids having said butyric to myristic weight ratio.

20. The process according to claim 14, wherein a weight ratio of butyric acid to myristic acid of the powdered milk solids is substantially equivalent to the weight ratio of butyric acid to myristic acid in the chocolate.

21. The process according to claim 14, further comprising adding myristic acid to the admixture.

22. The process according to claim 14, further comprising adding enzymatically modified milk fat, anhydrous milk fat, milk fat equivalents, or enzymatically modified butter to the admixture.

23. The process according to claim 14, wherein said weight ratio of butyric acid to myristic acid is achieved by direct addition of at least myristic acid to said admixture.

24. The process according to claim 14, wherein said weight ratio of butyric acid to myristic acid is achieved by addition to said admixture either (i) milk solids containing myristic acid or (ii) a myristic acid precursor.

25. A chocolate having a developed milk character prepared according to the process of claim 14.

26. The chocolate according to claim 25, wherein a concentration of amorphous sucrose in said chocolate is less than 3% by weight of total sucrose.

27. The chocolate according to claim 26, wherein said concentration of amorphous sucrose is in a range of about 1 to about 1.5% by weight of total sucrose.

28. A process for preparing chocolate having a developed milk flavor comprising the steps of (i) admixing a liquid milk with at least one of sugar, chocolate liquor, cocoa solids or cocoa butter to form a liquid chocolate precursor ingredient; (ii) modifying the liquid chocolate precursor ingredient to achieve a C4 to C14 ratio equal to or less than 1:2; (iii) drying the liquid chocolate precursor ingredient to form a dried chocolate precursor ingredient; and preparing the chocolate with the dried chocolate precursor ingredient.

29. The process according to claim 28, wherein said weight ratio of butyric acid to myristic acid is in a range of 1:2.5 to 1:100.

30. The process according to claim 28, wherein said weight ratio of butyric acid to myristic acid is in a range of 1:3 to 1:6.

31. The process according to claim 28, wherein sugar and chocolate liquor are admixed with the liquid milk.

32. The process according to claim 28, wherein said liquid milk is selected from the group consisting of (i) milk, (ii) reconstituted milk, (iii) partially reconstituted milk, (iv) evaporated milk, (v) condensed milk, (vi) recombined milk, (vii) skim milk containing one or more of milk fat, anhydrous milk fat, milk fat equivalents and butter, and (viii) mixtures thereof.

33. The process according to claim 28, wherein the step of drying comprises spray drying or freeze drying.

34. The process according to claim 28, wherein the step of modifying the liquid chocolate precursor ingredient comprises the direct addition of at least myristic acid thereto.

35. The process according to claim 28, wherein the step of modifying the liquid chocolate precursor ingredient comprises treating the liquid chocolate precursor ingredient to reduce an amount of butyric acid.

36. The process according to claim 35, wherein the step of treating the liquid chocolate precursor ingredient comprises vacuum distillation.

37. The process according to claim 28, wherein the step of modifying the liquid chocolate precursor ingredient comprises enzymatic modification.

38. The process according to claim 37, wherein enzymatic modification comprises contacting the liquid chocolate precursor ingredient with a microbial culture.

39. A chocolate having a developed milk character prepared according to the process of claim 28.

40. The chocolate according to claim 39, wherein a concentration of amorphous sucrose in said chocolate is less than 3% by weight of total sucrose.

41. The chocolate according to claim 39, wherein a concentration of amorphous sucrose in said chocolate is in a range of about 1 to about 1.5% by weight of total sucrose.

42. A process for preparing chocolate having a developed milk flavor comprising the step of direct addition of at least one milk fatty acid to a chocolate to obtain a free fatty acid profile in said chocolate wherein:
   (i) butyric acid in a range of about 5 ppm to about 876 ppm;
   (ii) caproic acid in a range of about 4 ppm to about 420 ppm;
   (iii) caprylic acid in a range of about 4 ppm to about 156 ppm;
   (iv) capric acid in a range of about 8 ppm to about 408 ppm;
   (v) lauric acid in a range of about 10 ppm to about 492 ppm; and
   (vi) myristic acid in a range of about 27 ppm to about 1752 ppm;
wherein the weight ratio of butyric acid to myristic acid is equal to or less than 1:2.

43. A chocolate prepared according to the process of claim 42.

44. A chocolate according to claim 43, wherein said free fatty acid profile comprises:
   (ii) butyric acid in a range of about 11 ppm to about 108 ppm;
   (ii) caproic acid in a range of about 9 ppm to about 89 ppm;
   (iii) caprylic acid in a range of about 8 ppm to about 77 ppm;
   (iv) capric acid in a range of about 17 ppm to about 186 ppm;
   (v) lauric acid in a range of about 19 ppm to about 192 ppm; and
   (vi) myristic acid in a range of about 55 ppm to about 545 ppm.

45. A process for preparing chocolate having a developed milk flavor comprising the step of adding at least one milk fatty acid to a chocolate ingredient used in said chocolate to obtain a free fatty acid profile in said chocolate wherein:
   (i) butyric acid in a range of about 5 ppm to about 876 ppm;
   (ii caproic acid in a range of about 4 ppm to about 420 ppm;
   (iii) caprylic acid in a range of about 4 ppm to about 156 ppm;
   (iv) capric acid in a range of about 8 ppm to about 408 ppm;
   (v) lauric acid in a range of about 10 ppm to about 492 ppm; and
   (vi) myristic acid in a range of about 27 ppm to about 1752 ppm;
wherein the ratio of butyric acid to myristic acid is equal to or less than 1:2.

46. A chocolate prepared according to the process of claim 45.

47. A chocolate according to claim 46, wherein said free fatty acid profile comprises:
   (i) butyric acid in a range of about 11 ppm to about 108 ppm;

(ii) caproic acid in a range of about 9 ppm to about 89 ppm;

(iii) caprylic acid in a range of about 8 ppm to about 77 ppm;

(iv) capric acid in a range of about 17 ppm to about 186 ppm;

(v) lauric acid in a range of about 19 ppm to about 192 ppm; and (vi) myristic acid in a range of about 55 ppm to about 545 ppm.

* * * * *